United States Patent [19]

Prior

[11] Patent Number: 4,510,800
[45] Date of Patent: Apr. 16, 1985

[54] DRILLING MUD TESTING SYSTEM HAVING A THERMALLY ISOLATED PUMP

[75] Inventor: Maurice Prior, Duncanville, Tex.

[73] Assignee: Mobil Oil Corporation, New York, N.Y.

[21] Appl. No.: 518,565

[22] Filed: Jul. 29, 1983

[51] Int. Cl.³ .............................................. G01N 25/00
[52] U.S. Cl. ........................................ 73/153; 73/61.4
[58] Field of Search ......................... 73/153, 61.4, 64.1, 73/55, 32 R, 53; 374/45; 417/379

[56] References Cited

U.S. PATENT DOCUMENTS

2,688,923  9/1954  Bonaventura et al. .............. 417/379
3,473,368  10/1969  Roper ............................... 73/61.4 X

Primary Examiner—Jerry W. Myracle
Attorney, Agent, or Firm—Alexander J. McKillop; Michael G. Gilman; Charles J. Speciale

[57] ABSTRACT

A system for testing drilling mud includes viscosity measuring tubes and other instruments for testing the parameters of drilling mud. The mud is heated to an elevated temperature and recirculates in a closed flow path which includes the measuring instrumentation. A diaphragm pump successively withdraws a column of mud from the flow path and discharges mud into the flow path to effect the recirculation. A pumping column between the flow path and the pump contains a column of drilling mud which thermally isolates the pump from the hot mud in the flow path.

10 Claims, 11 Drawing Figures

DRILLING MUD TESTING SYSTEM HAVING A THERMALLY ISOLATED PUMP

BACKGROUND OF THE INVENTION

This invention relates to a system for testing the parameters of drilling mud, and more particularly, to a pump which recirculates hot drilling mud in the testing system.

In the drilling of wells, such as oil or gas wells, by the rotary method, a drilling mud is circulated from the surface of the earth to the drill bit and back to the surface again for the purposes of cooling the drill bit, removing earth cuttings from the bore hole, and imposing a hydrostatic pressure on the drilled earth formations to prevent flow of fluid therefrom into the well bore hole. In a drilling mud containing water and clay, the rheological properties of plastic viscosity, gel strength, and yield point, which must be maintained within limits in order that the drilling fluid remain pumpable and perform its desired functions, depend largely upon the concentration of clay solids and the extent to which the clay solids are hydrated by and dispersed within the water contained in the fluid.

Drilling muds are used under a wide variety of conditions which require that different compositions be used. For example, where the well bore hole passes through formations containing clay, the clay admixes with the drilling mud and this clay is hydrated by and dispersed by the water in the drilling fluid, thereby increasing the concentration of dispersed clay solids. The increase in the concentration of dispersed clay solids deleteriously affects the rheological properties of the drilling mud. Accordingly, where control of rheological properties is important, the drilling mud should have a minimum change in such properties with increasing concentrations of clay solids.

Usually, drilling muds are thixotropic, i.e., they increase in viscosity at low shear rates and decrease in viscosity at high shear rates, whereby the cuttings may be readily separated from the drilling fluid at the surface of the earth and, in the event circulation of drilling fluid is stopped for any reason, the cuttings will be properly suspended by the drilling fluid within the well and not sink to the bottom thereof with resultant danger of sticking drill pipe. The thixotropic properties of a drilling mud are ordinarily imparted to it by employing a clay such as bentonite as one of the constituents. Since one of the functions of a drilling mud is to impose a hydrostatic pressure on the formations penetrated by the well, it is desirable that the drilling mud have the correct density, and density of a drilling mud is increased by adding thereto a weighting agent such as barite. Drilling muds also often contain caustic soda which is added to solubilize certain constituents, inhibit fermentation of organic additives, reduce the effect of contaminants picked up during drilling and to affect other results depending on the type of drilling mud being employed.

Another property desired in a drilling mud is that of resisting gelation at high temperature. With increasing depth of the well, the bottom hole temperature increases. In many wells, these temperatures exceed 300° F. With aqueous drilling muds, high temperatures induce cementation reactions between clay minerals and various drilling mud additives. As a result, the drilling mud tends to attain excessively high gel strengths. With gelation, excessively high pump pressures are required to break circulation with the result that often loss of the drilling mud occurs by being forced into permeable formations. Additionally, gelation of the drilling mud can prevent logging tools from reaching the bottom of the well.

Frequently, during the drilling of a well, drilling conditions change. Changes in temperature occur. The character of the formations being drilled may change, as for example, salt may be encountered. Each change in drilling conditions can affect the properties of the drilling mud. Frequently, to counteract the effect of the changed drilling conditions on the properties of the drilling mud, a change in the composition or character is required.

The foregoing and other considerations dictate that drilling muds be tested under conditions which closely approximate conditions which would be encountered during drilling. By adding different additives, and by subjecting the drilling mud to various conditions of temperature and pressure, a determination can be made as to whether the mud will perform adequately under actual drilling conditions.

A particular problem encountered in systems for testing drilling muds is pumping the hot, viscous mud under pressure through the instrumentation for testing its parameters.

It is an object of the present invention to provide a system with a diaphragm pump which pumps hot drilling mud in a closed recirculating loop and which is thermally isolated from the hot mud.

RELATED APPLICATIONS

The following related applications are incorporated herein by reference: Ser. No. 518,336, filed July 29, 1983, now U.S. Pat. No. 4,483,189 "FLUSHING APPARATUS FOR A DRILLING MUD TESTING SYSTEM", Seal; Ser. No. 518,568, filed July 29, 1983, "CONTROLLED HEATER FOR DRILLING MUD TESTING SYSTEM", Quigley and Russell; Ser. No. 518,569, filed July 19, 1983, "PREPARATION UNIT FOR A DRILLING MUD TESTING SYSTEM", Prior.

SUMMARY OF THE INVENTION

A system for testing drilling mud includes a heater for heating the drilling mud to an elevated temperature and instrumentation for measuring the viscosity and other parameters of the heated drilling mud. A diaphragm pump pumps the heated drilling mud in a closed flow path through the instrumentation. The pump successively withdraws mud from the flow path and discharges mud into the flow path. In accordance with the present invention, a water cooled pumping column between the diaphragm pump and the flow path contains a column of drilling mud which thermally isolates the temperature sensitive diaphragm of the pump from the heated drilling mud in the flow path.

The foregoing and other objects, features and advantages of the invention will be better understood from the following more detailed description and appended claims.

DESCRIPTION OF THE PREFERRED EMBODIMENT

Figures 1, 1A:
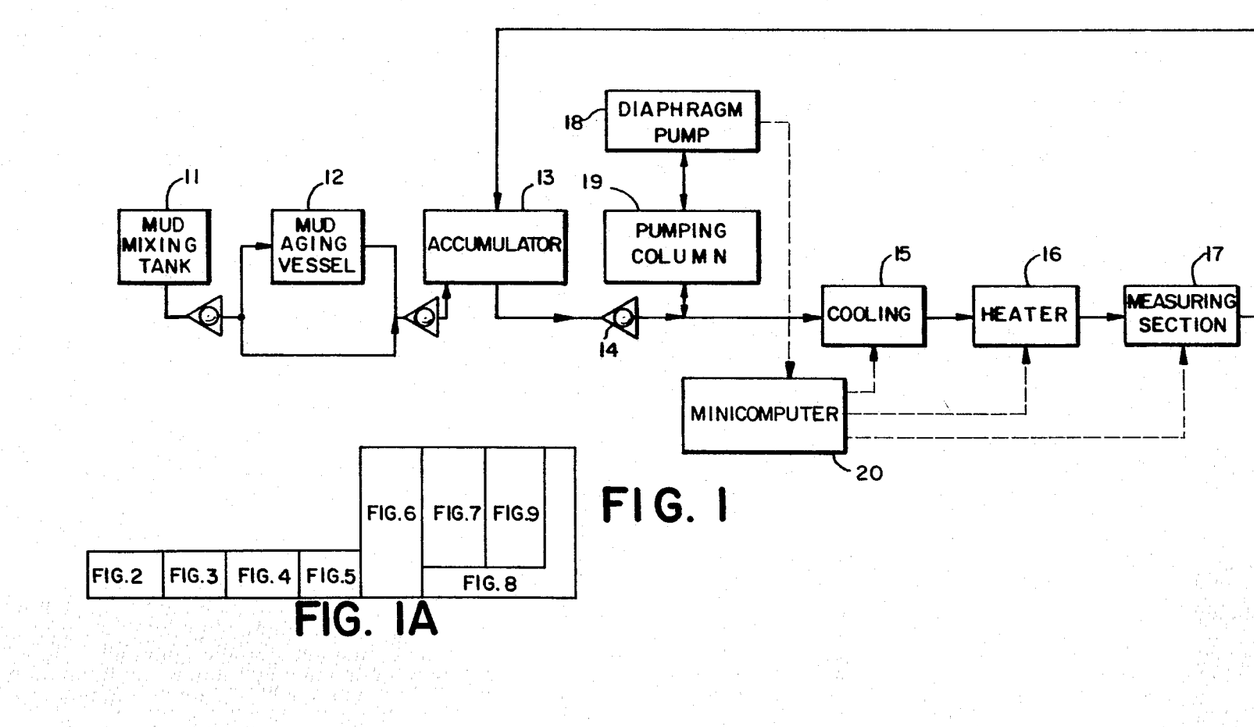
FIG. 1 shows the drilling mud testing system of the present invention.
FIG. 1A shows the manner in which FIGS. 2–9 fit together to show the details of the drilling mud testing system of the present invention.

Referring to FIG. 1, the system for testing drilling mud includes an open mixing tank 11 for mixing muds and additives, and an aging vessel 12 for aging the mud at high temperature and under pressure. An accumulator 13 pressurizes the drilling mud which circulates at the desired pressure.

Mud travels in the closed recirculating loop which includes check valve 14, cooling heat exchanger 15 and heater 16 which heats the drilling mud to an elevated temperature. The parameters of the mud are measured in the measuring section 17.

The mud is pumped in the closed loop by the diaphragm pump 18. Diaphragm pump 18 has diaphragms which are sensitive to temperature and must be protected from the high temperature of the drilling mud. In accordance with the present invention, a water cooled pumping column 19 isolates the diaphragm pump from the hot drilling mud in the flow path. The pump 18 successively withdraws mud from the flow path and discharges mud into the flow path. The column of mud in the water cooled pumping column 19 reciprocates therein, but hot mud never reaches the diaphragm pump 18.

The mud is pumped in the closed loop under control of minicomputer 20 which receives inputs indicating mud temperature, pressure and other parameters, and produces control signals controlling the operation of the system.

Figure 2:
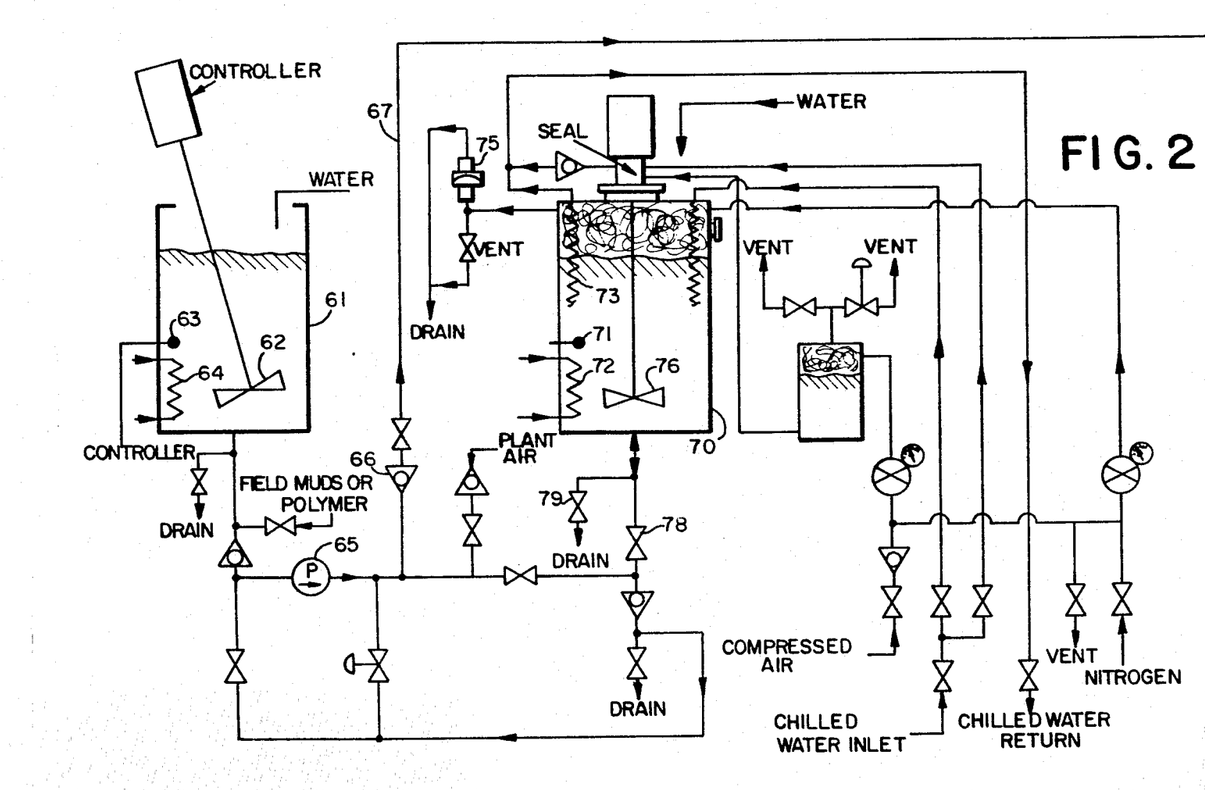
Figure 8:
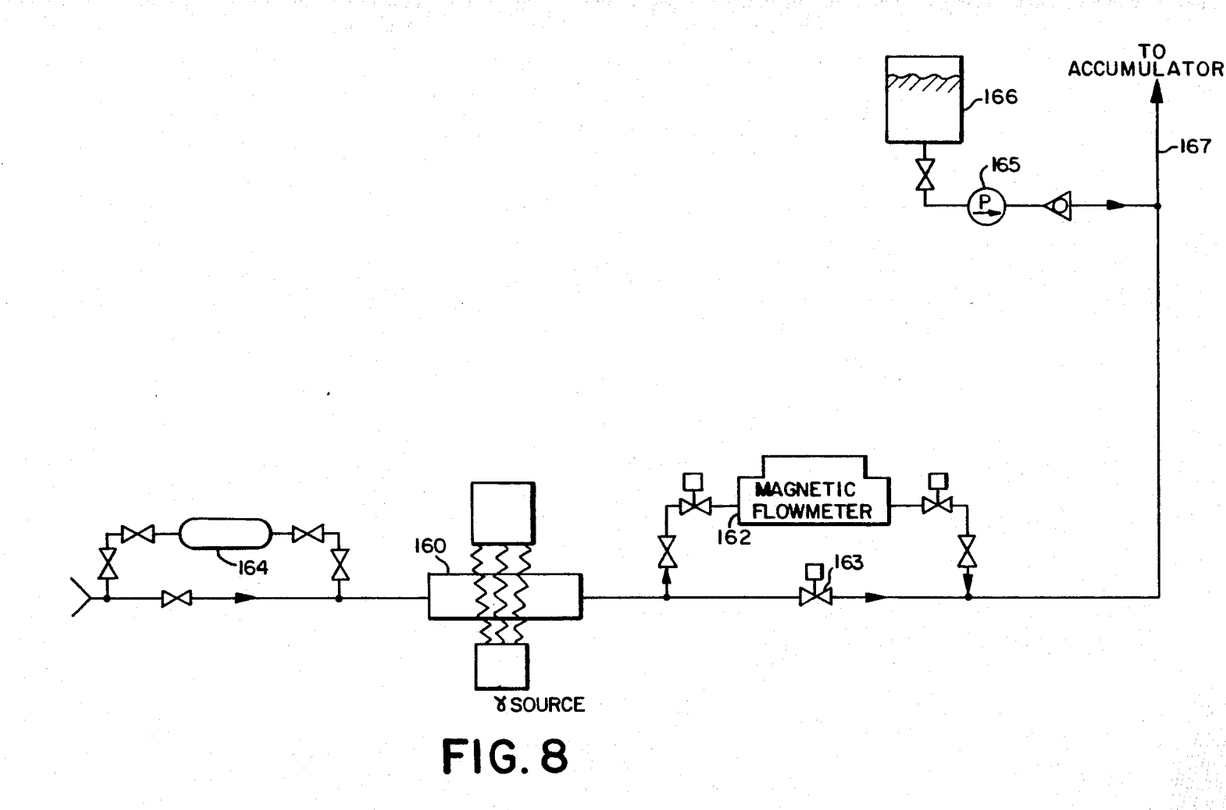
Figure 9:
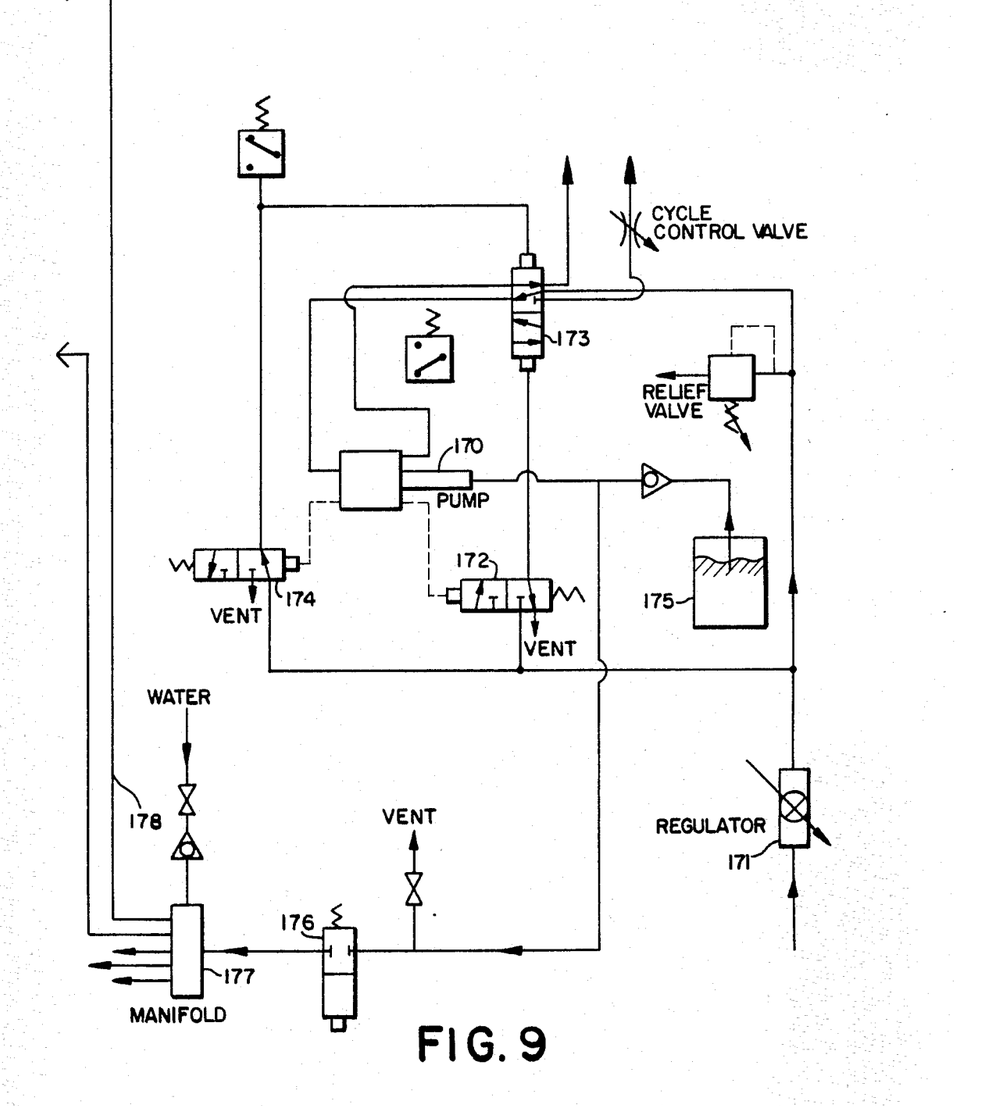
Figure 10:
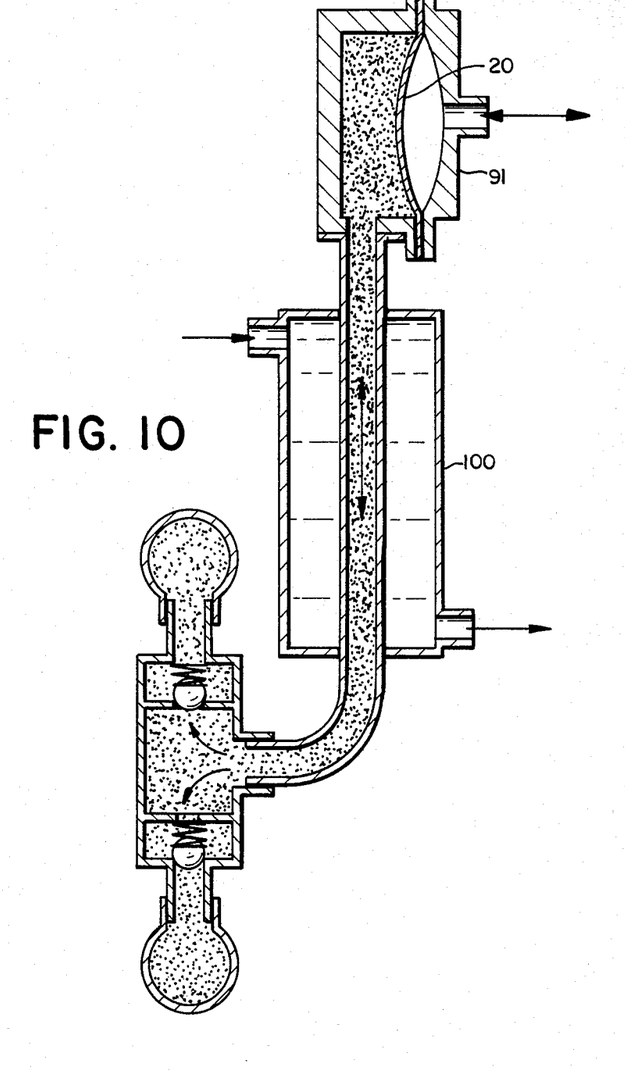
FIG. 10 depicts the manner in which the temperature-sensitive diaphragm of the pump is thermally isolated from the hot drilling mud.

The forgoing will be better understood from reference to FIGS. 2–9 which show the various components of the system, and FIG. 10 which show a pumping column and a pump diaphragm. FIG. 2 shows the mud preparation section of the system where the drilling mud is mixed and aged. Open mixing tank 61 is, for example, a tank of approximately 6 gallon capacity, which has a mixing paddle 62 for mixing drilling muds. Thermocouple 63 is connected to the mixing controller which, in turn, controls the heater 64. Transfer pump 65 is used to transfer mud directly into the system through check valve 66 and thence to the main loop 67. Alternatively, pump 65 transfers mud from mixing tank 61 to the aging vessel 70.

Aging vessel 70 is approximately a 6 gallon vessel. It maintains the mud at approximately 350° F. and under a pressure of 150 psi maximum. Thermocouple 71 is connected to the controller which in turn controls heater 72. Aging vessel 70 also includes cooling coil 73. Mixer 76 is provided to shear the mud and homogenize it. The mud is maintained under pressure in aging vessel 70 so that it does not boil at the aging temperature. When the mud has been properly aged, chilled water is supplied to the cooling coil 73 to cool the mud to the proper temperature. Mud is withdrawn from the aging vessel 70 through a screen in the bottom of the vessel, through valve 78 to the suction side of pump 65. Pump 65 pumps the mud through check valve 66 to the main loop 67.

A transfer pump is arranged in conjunction with the valves so that mud can be transferred only from the mixing tank to the aging vessel or to the main loop 67 of the system. Valving is also provided so that mud can be transferred from the aging vessel 70 only to the main loop of the system. Because of this, hot mud from the aging vessel can never be transferred to the open mixing tank 61. Once the mud is in the aging vessel 70, it can be discharged through valve 79 to drain, or it can be transferred to the main system. This is an important feature which prevents accidental spillage of hot mud which is quite undesirable.

Figure 3:
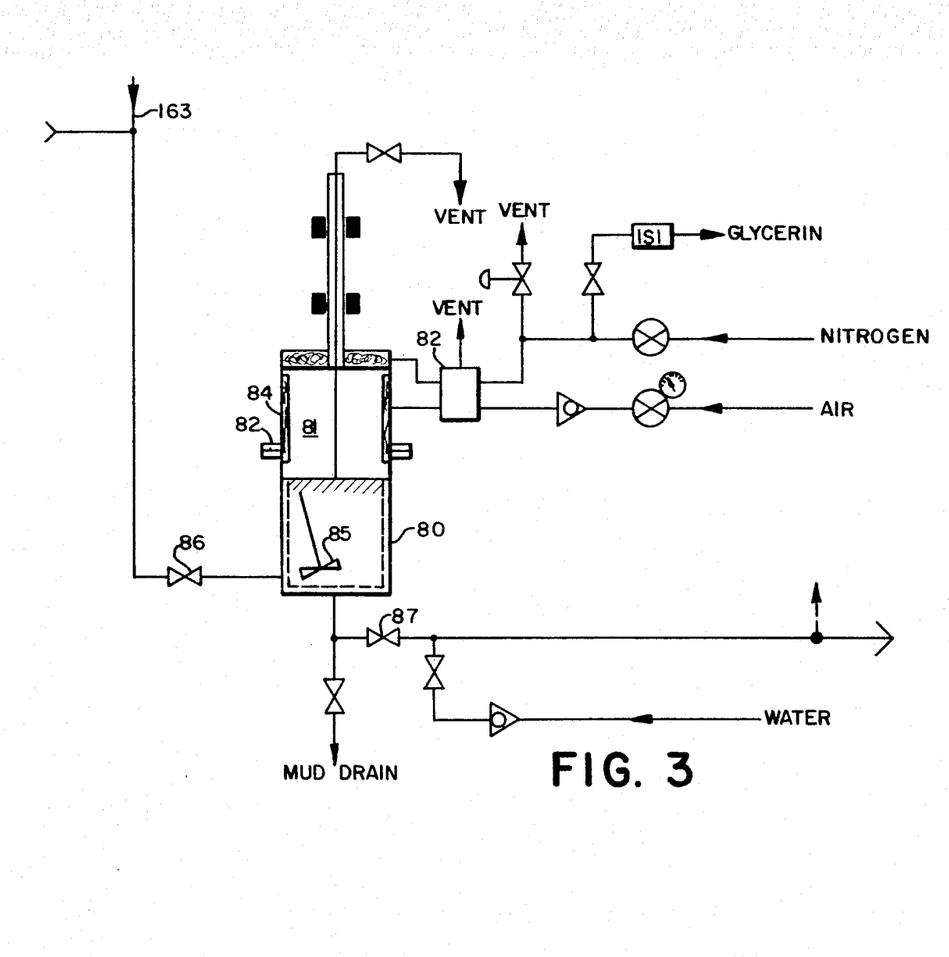

FIG. 3 shows the accumulator 80 which is used to pressurize the mud to 1500 psig maximum. A piston 81 in the top of the accumulator is driven by pressurized air or nitrogen supplied through a manifold valve. Accumulator 80 has a removable head to permit access to it. Flange 82 provides access to the accumulator. The accumulator is the invention claimed in my co-pending application Ser. No. 518,569, filed July 29, 1983, "PREPARATION UNIT FOR A DRILLING MUD TESTING SYSTEM".

When the system is to be pressurized, the head 84, including its piston, is moved on its counter-balanced suspension to place it over the accumulator 80. The threads of the flange 82 are tightened. Then, nitrogen gas pressure applied to the top side of the piston 81 pressurizes the mud, but at no time does gas reach the mud. This is important to prevent forcing gas into the mud.

The head of the accumulator is removable so that periodic inspection can be made of rings and the like to ensure that gas is not escaping into the mud. The seal on the accumulator ensures that the flange cannot be unlocked when the accumulator is under pressure, thereby preventing accidental mud spillage. Also, the removable head permits changes in the mud composition at reduced temperature and pressure during an experiment.

After the mud has been cooled to approximately 180° F., the flange 82 can be unlocked and the head can be removed. This allows addition of solid or liquid additives to the mud which is being tested. A portable mixer 85 in a wire basket can be inserted into the accumulator to provide proper mixing and then removed prior to replacing the head and operating the system.

When the head 84 of the accumulator is removed, the piston 81 can be driven downwardly by air so that the operator can inspect the piston for wear. The piston can then be driven back up into the head by air.

During operation, the mud flows into the accumulator through valve 86. It flows out of the accumulator through valve 87 to the suction side of the pump. The accumulator provides mud under a constant pressure to the pump.

Figure 4:
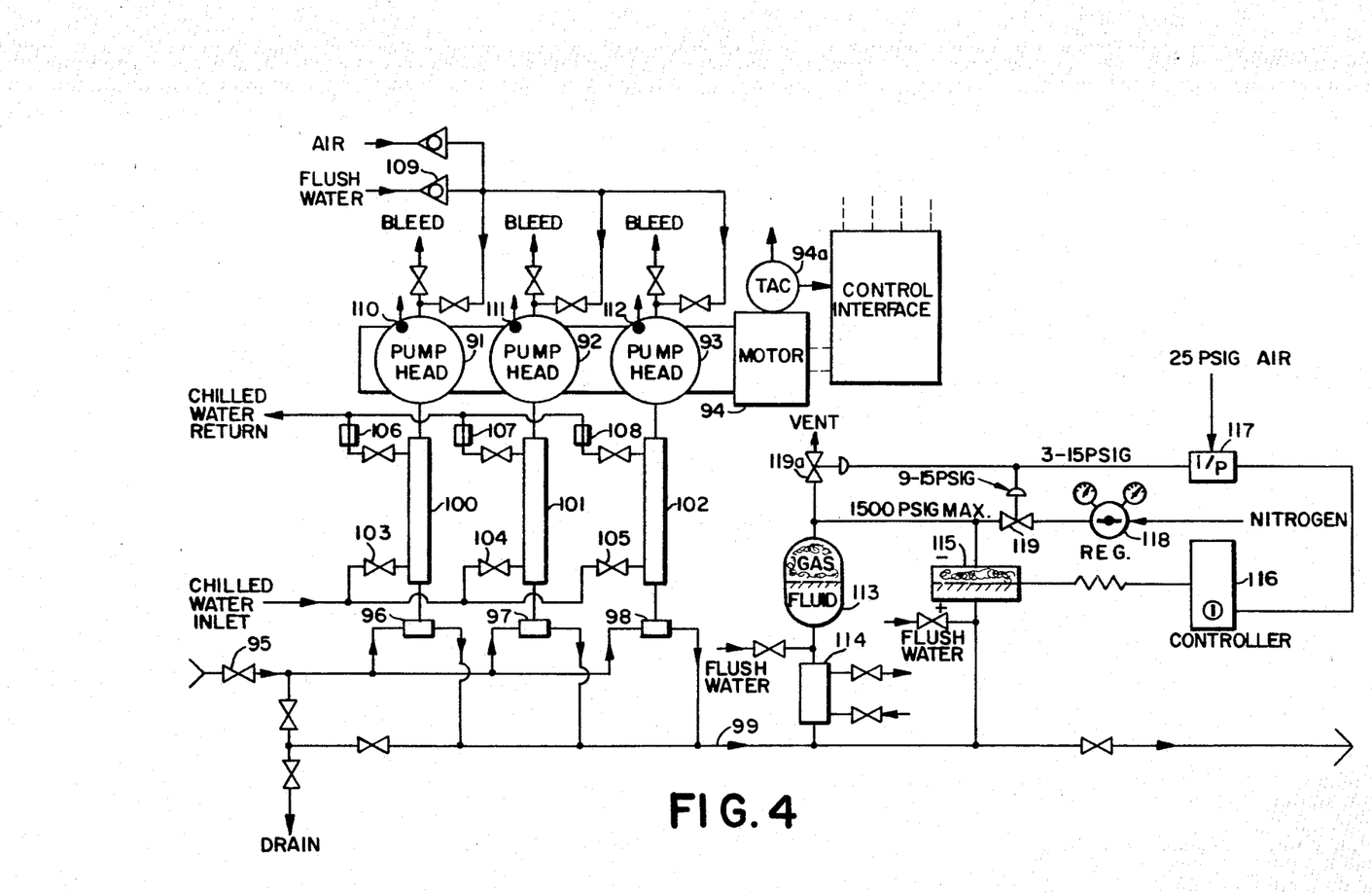

FIG. 4 shows the pump of the present invention. The pump includes pump heads 91, 92 and 93 driven by a common motor 94. The mud flow path is through valve 95 and through the double ball check valves 96–98. The line 99 leads to the cooling and heating section. On successive strokes of the diaphragm in each of the pump heads 91–93, mud is withdrawn from the flow path and discharged into the flow path through the check valves 96–98. There is a water cooled pumping column between pump head 91 and check valve 96, between pump head 92 and check valve 97, and between pump head 93 and check valve 98. Specifically, heat exchangers 100–102 contain a column of drilling mud which thermally isolates the heat sensitive diaphragms of the pumps 91–93 from the heated drilling mud in the flow path. Chilled water is supplied through solenoid valves 103–105 to the heat exchangers.

Flush water is supplied through check valve 109 to flush the diaphragms in the pump heads.

Thermocouples 110–112 detect any over temperature caused by the excursion of hot mud into the pump heads and operate an alarm which prevents damage to the diaphragms under this malfunction condition.

Pumps 91–93 are positive displacement diaphragm pumps which have diaphragms of an elastic material which will tolerate only 300° F. Since the circulating mud can be 500° F., these diaphragms must be protected from over temperature.

In order to dampen pulsations in the flow path 99, a pulsation dampener 113 is provided. It is connected through heat exchanger 114 to the flow path 99. The pulsation dampener 113 has a controllable pressure gas head. Transducer 115 senses the pressure differential between the flow path 99 and the gas head in pulsation dampener 113. The flow pulsations caused by the pumps 91–93 are dampened out by the pulsation dampener 113 when the correct pressure differential is maintained. The controller 116 provides electrical signals to the current/pressure transducer 117 which in turn supplies air pressure signals to the control valves 119 and 119a. These control valves alternately open and close as required to maintain the correct pressure differential between the flow path 99 and the gas head pulsation dampener 113. The desired pressure differential is set on controller 116. Nitrogen gas pressure is supplied to the pulsation dampener gas head 113 via the regulator 118 and control valve 119. Control valve 119a is used to vent excess nitrogen gas.

Figure 5:
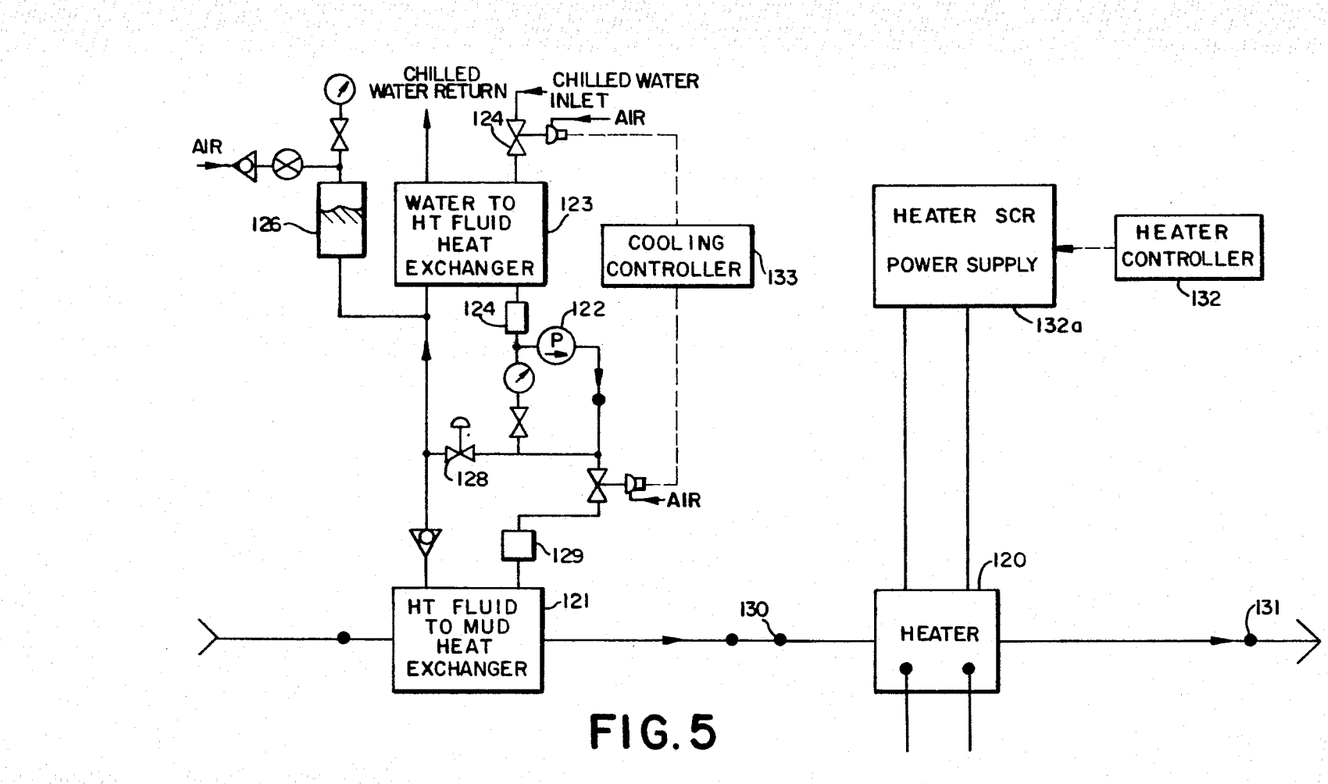

The heat exchange section is shown in FIG. 5. It includes a heater 120 which is the invention disclosed and claimed in application Ser. No. 518,568, filed July 29, 1983, "CONTROLLED HEATER FOR DRILLING MUD TESTING SYSTEM", Quigley and Russell. The system is arranged to maintain an approximately constant temperature increment across the heater 120. In order to provide rapid heating of the drilling mud initially, a large capacity heater is required. Such a large capacity heater cannot be used to efficiently control the temperature of the drilling mud after it has reached the desired temperature. This requires small changes in temperature when the system is operating, which would require turning heater elements on and off. In order to avoid this, the mud is first cooled in a heat exchanger 121 before it enters the heater. The cooling is relatively small, for example, from approximately 400° F. to 375° F. The heater 120 supplies a constant amount of heat to the slightly cooled mud.

A heat transfer fluid such as silicon oil, is the heat exchange medium in heat exchanger 121. Pump 122 circulates the heat transfer fluid between the heat exchanger 121 and the heat exchanger 123. Chilled water is supplied to heat exchanger 123 through the control valve 124. A reservoir 126 contains the heat transfer fluid.

Flow switch 127 is operated when the system is flowing properly. A back pressure regulator 128 and a flow meter 129 are provided to ensure proper flow of heat exchanger fluid through the heat exchanger 121.

Thermocouples 130 and 131 sense the temperature at the inlet and the outlet of heater 120. Heater controller 132 controls the heater power supply 132a to bring the mud temperature up to its desired level, for example, 400° F.

Thereafter, cooling controller 133 controls the cooling of the mud to maintain the temperature differential across the heater 120 at a constant value. For example, if a differential of 25° F. is to be maintained, the mud is cooled by heat exchanger 121 to approximately 375° F. so that this temperature differential can be maintained across the heater 120.

Figure 6:
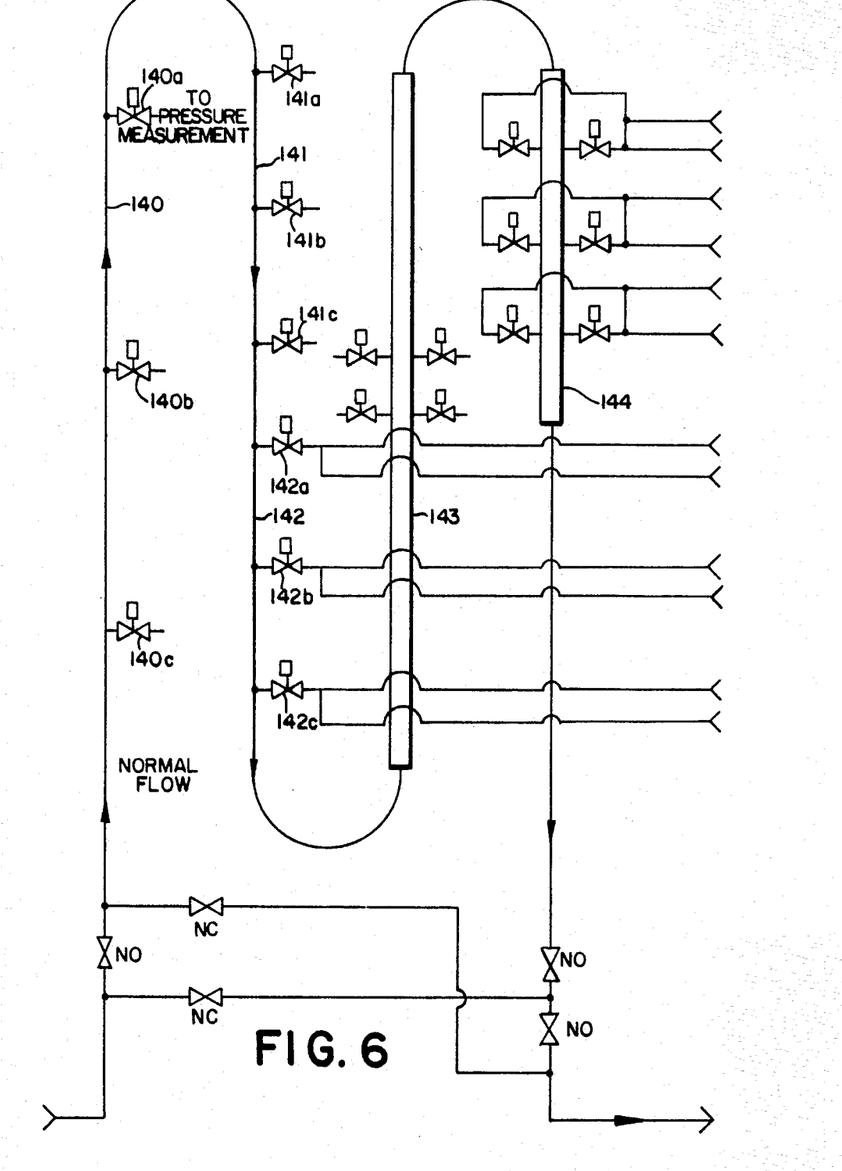

Referring to FIG. 6, the measuring section for testing the parameters of the drilling mud includes viscosity measuring tubes 140–144. Each viscosity measuring tube has three pressure measuring taps. Viscosity measuring tube 140 is, in the exemplary embodiment, a 0.495 inch inside diameter tube with pressure tape connected to the solenoid operated valves 140a, 140b, and 140c. A shear stress measurement is made automatically by opening two out of the three solenoid operated valves 140a–140c, thereby measuring the pressure drop across a short length of tube, such as between the valves 140c and 140b, or across a longer length of tube between valves 140c and 140a. Viscosity is calculated from the shear stress/shear rate relationship.

Similarly, viscosity measuring tube 141 is a 0.402 inch inside diameter tube with taps accessed by solenoid valves 141a–141c. Viscosity measuring tube 142 is a 0.311 inch inside diameter tube with three taps accessed by solenoid operated valves 142a–142c.

Viscosity measuring tubes 143 and 144 are annular tubes. Tube 143 has an outer tube with an inside diameter of 1.66 inches. It contains an inner tube with an outside diameter of 1½ inches. Tube 144 has an outer tube with an inside diameter of 0.62 inches and an inner tube with an outside diameter of 0.25 inches. Again, pressure is measured along a length between taps which are selected by solenoid operated valves. In this case, measurements are made in the annular space between the inner and outer tubes.

Annular viscosity measuring tubes 142 and 143 are provided with diametrically opposed pressure taps. If the inner tube is displaced, this may result in an erroneous pressure reading from a single tap. However, by using diametrically opposed taps, the pressure difference caused by displacement of the inner tube averages out.

Figure 7:
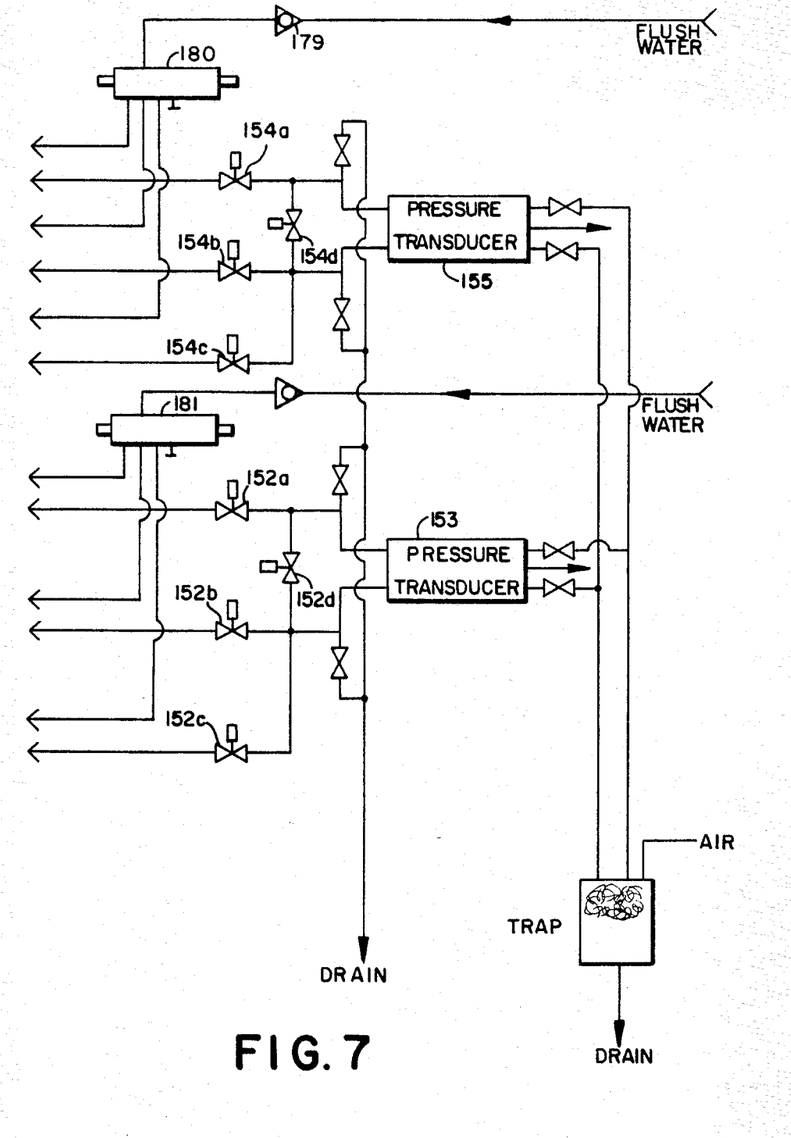

FIG. 7 shows the valving and manifolds for the viscosity measuring tubes 142 and 144 (FIG. 6). The valving and manifolds for the other three viscosity measuring tubes are similar. Referring first to the viscosity measuring tube 142, the pressure taps are connected through solenoid actuated valves 142a–c (FIG. 6) and 152a–d (FIG. 7) to the pressure transducer 153. Depending upon the actuation of these valves by the programmable controller, the pressure drop between two out of the three taps will be measured by the pressure transducer 153. Similarly, the three pressure taps on annular viscosity measuring tube 144 are connected through the solenoid operating valves 154a–d to the pressure transducer 155 which measures the pressure drop across the selected pressure taps of the viscosity measuring tube 144.

Referring to FIG. 8, the measuring section also includes a gamma source densitometer 160 that measures the density of the drilling mud. Flow meter 162 has valving which can be used to divert flow through the flow meter up to a temperature of 350° F. Above 350° F., flow is through the valve 163. Above 350° F. the tachometer 94a (FIG. 4) on the pump 94 is used to indicate flow through the system. Since pump heads 91–93 are positive displacement pumps, each stroke pumps a precise volume of drilling mud through the system. Therefore, the tachometer output provides a reliable measurement of flow through the system.

The flow of drilling mud can be diverted through the sample cell 164 (FIG. 8) to collect a sample of drilling mud therein. Flow is then returned to the normal path and desired measurements can be made on the drilling mud in the sample cell.

Pump 165 supplies additives from the reservoir 166 to the system. For example, a caustic such as sodium hydroxide is injected into the flow stream to maintain a high pH. Line 167 is connected to the line 167 in FIG. 3 to complete the closed loop system.

FIG. 9 shows the fluid flush pump 170 which is used to periodically flush certain points in the system with clean water. The flush pump is more fully described and claimed in co-pending application Ser. No. 518,336, filed July 29, 1983 "FLUSHING APPARATUS FOR A DRILLING MUD TESTING SYSTEM", Seal. Pump 170 has a piston which is actuated by pressurized air supplied through regulator 171. Slide valves 172-174 control the flow of air to both sides of the piston to actuate it in strokes which pressurize flush water from reservoir 175 to a pressure of approximately 1500 psi. The pressurized water is supplied through valve 176 to the manifold 177 which distributes it to the various taps of the viscosity measuring tubes and to other points in the system which are to be flushed with clean water. For example, flush water is supplied through line 178 and through check valve 179 (FIG. 7) and line select valve 180 to the taps of the annular viscosity measuring tube 144 (FIG. 6).

FIG. 7 also shows the line select valve 181 for supplying flush water to the taps of viscosity measuring tube 142 (FIG. 6). Similar flushing is provided for the other viscosity measuring tubes.

FIG. 10 depicts the diaphragm 20 in the pump head 91. Diaphragm 20 successively draws a column of drilling mud upward through heat exchanger 100 and then discharges the column downwardly into the flow path. Because of the check valves in the flow path, the mud is circulated in the flow path. The column of mud in the heat exchanger 100 thermally isolates the diaphragm 20 from the hot drilling mud in the flow path.

While a particular embodiment of the invention has been shown and described, various modifications are within the true spirit and scope of the invention. The appended claims are, therefore, intended to cover all such modifications.

What is claimed is:

1. A system for testing drilling mud comprising:
   measuring means for testing the parameters of said drilling mud;
   means for heating said drilling mud to an elevated temperature; and
   means for pumping heated drilling mud through a flow path to said measuring means including:
   a pump which successively withdraws mud from said flow path and discharges mud into said flow path;
   a pumping column between said flow path and said pump, said column containing drilling mud which thermally isolates said pump from the heated drilling mud in said flow path; and
   a heat exchanger between said flow path and said pump for cooling drilling mud therein, said drilling mud reciprocating in said pumping column as said pump successively withdraws and discharges said mud.

2. The system recited in claim 1 wherein said pump is a diaphragm pump having a heat-sensitive diaphragm.

3. The system recited in claim 2 wherein said pump is a plastic diaphragm pump.

4. The system recited in claim 1 further comprising:
   a pulsation dampener connected to said flow path to suppress pressure variations in said flow path caused by the successive withdrawal and discharge of mud to said flow path.

5. The system recited in claim 4 wherein said pulsation dampener has a controllable pressure gas head;
   a transducer for sensing pressure changes in said flow path; and
   a regulator responsive to said transducer for controlling said gas head to maintain pressure variations at a desired level.

6. The system recited in claim 1 wherein said pump has multiple pump heads each having a diaphragm driven by a common motor.

7. The system recited in claim 6 wherein said heat exchanger comprises:
   a water cooled pumping column between each pump head and said flow path.

8. The system recited in claim 1 wherein said flow path is a closed recirculating loop.

9. The system recited in claim 8 further comprising:
   a check valve in said flow path in front of said pump to provide flow in one direction in said loop.

10. The system recited in claim 1 further comprising:
    a temperature sensor in said pump; and
    an alarm actuated by said temperature sensor when the temperature in said pump exceeds a given level.

* * * * *